(12) United States Patent
Yamamoto et al.

(10) Patent No.: US 9,700,394 B2
(45) Date of Patent: Jul. 11, 2017

(54) DENTAL ULTRASONIC CLEANING DEVICE AND METHOD FOR CLEANING TEETH OR DENTURES BY USING ULTRASONIC WAVES

(71) Applicants: Matsuo Yamamoto, Tokyo (JP); Takashi Takiguchi, Tokyo (JP); Masanori Sato, Aichi (JP); Katsuyuki Inagaki, Aichi (JP); Kazumasa Kubota, Aichi (JP); Hideo Kozaka, Aichi (JP); Toshiaki Miyamoto, Aichi (JP)

(72) Inventors: Matsuo Yamamoto, Tokyo (JP); Takashi Takiguchi, Tokyo (JP); Masanori Sato, Aichi (JP); Katsuyuki Inagaki, Aichi (JP); Kazumasa Kubota, Aichi (JP); Hideo Kozaka, Aichi (JP); Toshiaki Miyamoto, Aichi (JP)

(73) Assignees: SHOWA UNIVERSITY, Tokyo (JP); HONDA ELECTRONICS CO., LTD., Aichi (JP); GC CORPORATION, Tokyo (JP)

( * ) Notice: Subject to any disclaimer, the term of this patent is extended or adjusted under 35 U.S.C. 154(b) by 236 days.

(21) Appl. No.: 14/404,459

(22) PCT Filed: Apr. 26, 2013

(86) PCT No.: PCT/JP2013/062470
§ 371 (c)(1),
(2) Date: Nov. 27, 2014

(87) PCT Pub. No.: WO2013/179842
PCT Pub. Date: Dec. 5, 2013

(65) Prior Publication Data
US 2015/0111169 A1 Apr. 23, 2015

(30) Foreign Application Priority Data
May 31, 2012 (JP) ................................ 2012-124622

(51) Int. Cl.
*A61C 1/07* (2006.01)
*A61C 17/20* (2006.01)
*A61C 17/02* (2006.01)

(52) U.S. Cl.
CPC .......... *A61C 17/20* (2013.01); *A61C 17/0202* (2013.01); *A61C 17/0208* (2013.01)

(58) Field of Classification Search
CPC .. A61C 17/20; A61C 17/0202; A61C 17/0208
(Continued)

(56) References Cited

U.S. PATENT DOCUMENTS 3,067,447 A * 12/1962 Birch ................... A46B 5/0012
15/167.1
4,299,221 A * 11/1981 Phillips .................. A61C 17/04
433/100
(Continued)

FOREIGN PATENT DOCUMENTS

CN 2294703 10/1998
DE 102 35 136 2/2004
(Continued)

*Primary Examiner* — Matthew Nelson
(74) *Attorney, Agent, or Firm* — Clark & Brody

(57) ABSTRACT

Provided is a dental ultrasonic cleaning device that efficiently cleans teeth or dentures in an oral cavity using ultrasonic waves. A dental ultrasonic cleaning device 1 emits ultrasonic waves through a cleaning-liquid (W1) to the surface of a cleaning-target 26, ultrasonically cleaning it. An ultrasonic horn 24 propagates ultrasonic waves being generated by an ultrasonic-wave transducer 23 and emits them from the vibratory surface 25 provided at the tip-end of the horn 24. A liquid-reserving part 27 is provided, surrounding the vibratory surface 25 of the ultrasonic horn 24, which (Continued)

temporarily reserves the cleaning-liquid (W1) between the vibratory surface 25 and the cleaning-target 26. A cap-member 33 is provided at a certain interval opposite the liquid-reserving part 27. A cleaning-liquid discharge-tube inlet 35 is connected to a vacuum tube 36 within the cap-member 33, allowing the cleaning-liquid W1 used during the ultrasonic cleaning to be vacuumed from the oral cavity, into the cap-member 33, and then discharged through the vacuum tube 36.

3 Claims, 3 Drawing Sheets

(58) Field of Classification Search
USPC ......... 433/216, 80, 27, 89, 82, 215, 86, 119, 433/115, 118, 91
See application file for complete search history.

(56) References Cited

U.S. PATENT DOCUMENTS

| | | | | |
|---|---|---|---|---|
| 4,417,874 | A * | 11/1983 | Andersson | A61C 17/043 433/96 |
| 5,432,971 | A * | 7/1995 | Chung | A46B 5/0012 15/144.1 |
| 6,152,733 | A * | 11/2000 | Hegemann | A61C 17/22 433/216 |
| 6,602,071 | B1 | 8/2003 | Ellion et al. | |
| 7,082,638 | B2 * | 8/2006 | Koh | A46B 9/045 15/167.2 |
| 7,849,548 | B2 | 12/2010 | Bock | |
| 2002/0183774 | A1 * | 12/2002 | Witt | A61B 17/32009 606/169 |
| 2003/0073054 | A1 * | 4/2003 | Van Hale | A61C 1/08 433/91 |
| 2005/0014107 | A1 * | 1/2005 | Culver | A61C 17/043 433/95 |
| 2005/0175960 | A1 * | 8/2005 | Wiek | A61C 17/222 433/88 |
| 2006/0008764 | A1 * | 1/2006 | Abo | A61C 17/043 433/95 |
| 2007/0184404 | A1 * | 8/2007 | Johnki | A61C 17/0211 433/80 |
| 2008/0280260 | A1 * | 11/2008 | Belikov | A46B 11/002 433/215 |
| 2009/0208898 | A1 * | 8/2009 | Kaplan | A46B 9/045 433/80 |
| 2009/0226241 | A1 * | 9/2009 | McEwen | A46B 9/025 401/268 |
| 2011/0262879 | A1 | 10/2011 | Hegemann | |
| 2012/0064480 | A1 | 3/2012 | Hegemann | |
| 2012/0077143 | A1 * | 3/2012 | Fougere | A46B 9/045 433/82 |
| 2013/0236851 | A1 * | 9/2013 | McDonough | A61C 17/0208 433/89 |

FOREIGN PATENT DOCUMENTS

| | | |
|---|---|---|
| JP | 59-125556 | 7/1984 |
| JP | 2001-008736 | 1/2001 |
| JP | 2006-075775 | 3/2006 |
| JP | 2006-101941 | 4/2006 |
| WO | 96/12447 | 5/1996 |
| WO | 2007/071031 | 6/2007 |
| WO | 2012/054905 | 4/2012 |

* cited by examiner

DENTAL ULTRASONIC CLEANING DEVICE AND METHOD FOR CLEANING TEETH OR DENTURES BY USING ULTRASONIC WAVES

TECHNICAL FIELD

This invention relates to a dental ultrasonic cleaning device and a method for cleaning teeth or dentures by an emission of ultrasonic waves through a cleaning-liquid to a surface of the teeth or dentures in an oral cavity.

TECHNICAL BACKGROUND

Regarding dental treatment, an ultrasonic scaler is now practically used for removing plaque or the like by using ultrasonic vibration. In the oral cavity, a bacterium grows proliferously on an exposed portion of the dental implant or the like. When cleaning the exposed portion by an ultrasonic scaler, a vibratory chip of the ultrasonic scaler may touch with the surface of the implant, and the erosion of the exposed portion conversely goes from bad to worse by the touching.

To resolve such a problem, an ultrasonic cleaning device is suggested (for example as shown in Patent Documents 1 and 2) for cleaning the surface of teeth or dentures in a non-contact manner by propagating ultrasonic waves through a cleaning-liquid. Patent Document 1 shows an ultrasonic cleaning device in which a cleaning-liquid is supplied to a nozzle consisting of an ultrasonic-emitting surface. The nozzle tip-end touches the surface of the teeth or the like, and the cleaning-liquid is discharged through it, thus forming a channel for the propagating ultrasonic waves. The ultrasonic cleaning device has different functions, i.e. a cleaning-liquid reserving mode for reserving the liquid within the nozzle, an ultrasonic cleaning mode, and a high-pressure cleaning mode are performed repeatedly for efficient cleaning.

Patent Document 2 shows an ultrasonic cleaning device in which a concaved part for reserving the liquid is provided in the center of a head on which the brush is placed. An ultrasonic transducer is provided adjacently at the bottom of the concaved part. The concaved liquid-reservoir part comprises a liquid-outlet for supplying the liquid and a discharge inlet for discharging the liquid.

PRIOR ART DOCUMENTS

Patent Documents

Patent Document 1: Japanese Patent No. 4349245
Patent Document 2: Japanese Patent No. 3534237

SUMMARY OF THE INVENTION

Problems to be Resolved by the Invention

The ultrasonic cleaning device as described in Patent Document 1 is not provided with a liquid-discharging device for discharging reserved liquid in the oral cavity during ultrasonic cleaning. In this case, being that it is necessary to remove the liquid from the oral cavity regularly, the places for using such an ultrasonic cleaning device is limited to a nearby sink or the like to allow for the reserved liquid in the oral cavity to be spit out, or to a dental operatory or the like having special liquid-removal equipment.

In using the ultrasonic cleaning device of Patent Document 1, it is possible to clean ultrasonically the surface of teeth or dentures near the discharge outlet of the nozzle even if the volume of the cleaning-liquid is fairly small. However, when ultrasonically cleaning embrasures (of teeth or dentures), it is necessary to increase the volume of the cleaning-liquid being supplied to make it spurt out from the discharge outlet of the nozzle. In high-pressure cleaning mode for washing out the dirt after an ultrasonic cleaning, a large volume of cleaning-liquid is supplied in the oral cavity, thus necessitating that the water-removal equipment discharge the water more frequently, thus eventually increasing the cost of discharging the water.

The ultrasonic cleaning device as described in Patent Document 2 above, is provided with a liquid-discharge inlet on the concaved water-reserving part of the device, thus making it possible during the cleaning of the oral cavity to discharge the reserved cleaning-liquid through the discharge spout. A liquid outlet is also provided on the concaved liquid-reservoir part, and the liquid being supplied from the liquid outlet and reserved in the concaved part flows along the surface of the teeth or dentures and then is discharged through the discharge spout. Therefore, when using the ultrasonic cleaning device of Patent Document 2, it is possible to clean the surfaces (of the teeth or dentures) opposite the concaved part of the device by the effect of the ultrasonic waves. Contrarily, the ultrasonic waves are unlikely to be effective within the embrasures of the teeth or dentures, thus making it difficult to remove contamination such as plaque or the like from between the teeth or dentures efficiently. Also, the ultrasonic cleaning device of Patent Document 2 is configured so as to be surrounded by a brush between the concaved liquid-reservoir part of the device and the surface of the teeth, at which time the cleaning-liquid seeps out from between the bristles of the brush, thus making it difficult to intervene the cleaning-liquid between the ultrasonic-wave transducer of the cleaning device and the surface of the teeth without securing a certain volume of supplied cleaning-liquid. Also, as the cleaning-liquid seeps out from between the bristles of the brush, air intervenes between the ultrasonic transducer and the surface of the teeth, thus rendering the ultrasonic waves ineffective to the surface of the teeth and the cleaning of the teeth insufficient.

This invention was achieved in light of the foregoing circumstances to provide a dental ultrasonic cleaning device and method for cleaning teeth or dentures efficiently in the oral cavity by using ultrasonic waves.

Means for Solving the Problems

To solve the aforementioned problems, the first aspect of this invention refers to a dental ultrasonic cleaning device for cleaning the teeth or dentures ultrasonically by emitting ultrasonic waves through a cleaning-liquid to a cleaning-target, such as a surface of teeth or dentures in an oral cavity, which is characterized by an ultrasonic-wave transducer for generating the ultrasonic waves; by an ultrasonic-wave propagating unit for propagating the ultrasonic waves to an ultrasonic-wave emitting surface at a tip-end side of the ultrasonic-wave propagating unit; by a liquid-reservoir part for temporarily reserving the cleaning-liquid between a surface of the cleaning-target and the ultrasonic-wave emitting surface in a state of being in contact with the cleaning target, the liquid-reservoir part being provided in such a manner as to surround the ultrasonic-wave emitting surface; by a liquid-supply tube for supplying the cleaning-liquid to the liquid-reservoir part; by a suction tube having a liquid-suction part and for sucking and draining the cleaning-liquid that had been used during the ultrasonic cleaning through the liquid-suction part, the liquid-suction part being disposed at a predetermined distance from the liquid reservoir part.

The first aspect of this invention allows for the cleaning-liquid within the liquid-reservoir part to be supplied there through the liquid-supply tube and temporarily reserved between the ultrasonic-wave emitting surface at the tip-end of the ultrasonic-wave propagating unit and the surface of the cleaning-target. The ultrasonic waves being generated by the ultrasonic-wave transducer are transferred through the ultrasonic-wave propagating unit and emitted from the ultrasonic-wave emitting surface through the cleaning-liquid within the liquid-reservoir part to the surfaces of the cleaning-target, thus ultrasonically cleaning them. The cleaning goes into the embrasures of the teeth or dentures as the cleaning-target and then is vacuumed by the cleaning-liquid vacuuming part provided behind the cleaning-target and then is discharged out of the oral cavity through the suction tube, at which time the ultrasonic waves propagating through the cleaning-liquid are efficiently working in the embrasures cleaning the sides of the cleaning-target as well.

The second aspect of this invention refers to a dental ultrasonic cleaning device according to the first aspect, comprising a handpiece to be handled by an operator, the handpiece comprising a main-arm unit to house the ultrasonic-wave transducer and the ultrasonic-wave propagating unit, and a secondary-arm unit having a tip-end portion by which the cleaning-target is gripped between the liquid-reservoir part at a tip-end of the main-arm unit, and the liquid-vacuuming part is provided at the tip-end of the secondary-arm unit.

The second aspect of this invention allows for the ultrasonic-wave transducer and the ultrasonic-wave propagating unit to be stored within the main-arm unit and for the cleaning-liquid vacuuming part to be at the tip-end of the secondary-arm unit. Thus, the liquid-reservoir part provided at the tip-end of the ultrasonic-wave emitting surface of the ultrasonic-wave propagating unit of the main-arm unit faces the cleaning-liquid vacuuming part provided at the tip-end of the secondary-arm unit. An operator such as a dentist or the like handles the handpiece so as to operate the main and secondary arms to grip the cleaning-target between the liquid-reservoir part at the tip-end of the main-arm unit and the cleaning-liquid vacuuming part at the tip-end of the secondary-arm unit. Even in pressing the liquid-reservoir part to the cleaning-target with a certain amount of pressure, such pressure is oppositely supported by the tip-end (cleaning-liquid vacuuming part) of secondary-arm unit, thus avoiding the problem of the cleaning-target moving due to the one-way pressure against the cleaning-target. Also, the main and secondary-arm units can be handled single-handedly by the operator in gripping the cleaning-target, thus improving operability of the cleaning device, thus conducting securely the ultrasonic cleaning.

The third aspect of this invention refers to a dental ultrasonic cleaning device according to the second aspect, characterized by an ultrasonic-wave oscillator for activating the ultrasonic-wave transducer; by a cleaning-liquid supplying device for supplying the cleaning-liquid to the liquid-supply tube; by a cleaning-liquid vacuuming-and-discharging device for vacuuming and discharging the cleaning-liquid through the suction tube; by a sensing-means for detecting the cleaning-target being gripped by and between the liquid-reservoir part of the main-arm unit and the cleaning-liquid vacuuming part at the tip-end of the secondary-arm unit; by a control device for controlling at least one of following three devices: the ultrasonic-wave oscillator, the cleaning-liquid supplying device, or the cleaning-liquid vacuuming-and-discharging device, according to the detection by the sensing-means.

The third aspect of this invention allows for the sensing-means to detect the cleaning-target being gripped by the liquid-reservoir part of the main-arm unit and the cleaning-liquid vacuuming part at the tip-end of the secondary-arm unit. Then, according to the detection by the sensing-means, at least one of the following three devices: the ultrasonic-wave oscillator, the cleaning-liquid supplying device, or the cleaning-liquid vacuuming-and-discharging device is activated by the control device, thus making it possible directly to clean the cleaning-target ultrasonically upon it being gripped.

The fourth aspect of this invention refers to a dental ultrasonic cleaning device, according to the second or third aspects, characterized in that the handpiece has a stapler structure that the base-end of the secondary-arm unit is rotatably connected to the main-arm unit.

The fourth aspect of this invention allows for the operator to hold and rotate the handpiece single-handedly in gripping the cleaning-target by and between the liquid-reservoir part of the main-arm unit and the cleaning-liquid vacuuming part at the tip-end of the secondary-arm unit.

The fifth aspect of this invention refers to a dental ultrasonic cleaning device according to the fourth aspect, whereof the sensing-means detects the rotation-angle of the secondary-arm unit and transmits the detection result to the control device for it to activate the ultrasonic-wave oscillator and the cleaning-liquid supplying device and the cleaning-liquid vacuuming-and-discharging device when the rotation-angle of the secondary-arm unit is below the set value, or to deactivate them when the rotation-angle of the secondary-arm unit exceeds the set value.

The fifth aspect of this invention allows for the rotation-angle of the secondary-arm unit whilst it is gripping the cleaning target to be detected by the sensing-means and for the sensing-means to transmit the result of detection to the control device. When the rotation-angle of the secondary-arm unit is below the set value, the ultrasonic-wave oscillator, the cleaning-liquid supplying device and the cleaning-liquid vacuuming-and-discharging device are activated. However, when the rotation-angle of the secondary-arm unit exceeds the set value, the ultrasonic-wave oscillator, the cleaning-liquid supplying device and the cleaning-liquid vacuuming-and-discharging device are deactivated. In this case, in rotating the handpiece so that the cleaning-target is gripped by and between the liquid-reservoir part of the main-arm unit and the cleaning-liquid vacuuming part of the secondary-arm unit, it is possible directly to start the ultrasonic cleaning. In releasing the grip of the cleaning-target, it possible directly to stop the ultrasonic cleaning. As such, without the cleaning-target being gripped, the ultrasonic cleaning will never start wrongly, thus reducing wastage of electricity and of cleaning-liquid and avoiding the problem of the ultrasonic waves being emitted to another area than that of the cleaning-target.

The sixth aspect of this invention refers to a dental ultrasonic cleaning device according to any one of the first to fifth aspects, characterized by a cleaning-liquid discharge-tube inlet being provided within or near the liquid-reservoir part and through which the cleaning-liquid is discharged from the liquid-reservoir part.

The sixth aspect of this invention allows for the cleaning-liquid to be discharged from the oral cavity through the cleaning-liquid discharge-tube inlet provided within or near the liquid-reservoir part provided at the tip-end of the main-arm unit whenever the cleaning-liquid cannot be discharged into the cleaning-liquid vacuuming part provided at the tip-end of the secondary-arm unit through the suction tube, thus avoiding the problem of too much cleaning-liquid collecting in the oral cavity, which would discomfort the subject during the ultrasonic cleaning.

The seventh aspect of this invention refers to a dental ultrasonic cleaning device according to the sixth aspect, characterized by a cleaning-liquid discharging device for discharging the cleaning-liquid through the cleaning-liquid discharge tube; by a cleaning-liquid supply-measuring device for measuring the volume of cleaning-liquid being supplied per hour through the liquid-supply tube; and by a cleaning-liquid discharge-measuring device for measuring the volume of cleaning-liquid being discharged per hour through the suction tube; and characterized in that the ultrasonic-wave control device reads the data of the cleaning-liquid supply-measuring device about the volume of cleaning-liquid being supplied and the data of the cleaning-liquid discharge-measuring device about the volume of cleaning-liquid being discharged, which then directs the operation of the cleaning-liquid vacuuming-and-discharging device according to the ratio of the volume of cleaning-liquid being supplied to the volume of cleaning-liquid being discharged.

The seventh aspect of this invention allows for the cleaning-liquid supply-measuring device to measure the volume of cleaning-liquid being supplied per hour through the liquid-supply tube and for the cleaning-liquid discharge-measuring device to measure the volume of cleaning-liquid being discharged per hour through the vacuum tube. The cleaning-liquid discharging device works according to the ratio of the volume of cleaning-liquid being supplied to the volume of cleaning-liquid being discharged, and then is discharged through the cleaning-liquid discharge tube. As such, when the volume of cleaning-liquid being discharged is less than the volume of cleaning-liquid being supplied, it is detected by the cleaning-liquid discharging device that the cleaning-liquid cannot be fully discharged only by the cleaning-liquid vacuuming-and-discharging device, in which case the cleaning-liquid can be discharged from the oral cavity through the cleaning-liquid discharge-tube by activating the cleaning-liquid vacuuming-and-discharging device, thus avoiding the problem of too much cleaning-liquid collecting in the oral cavity, which would discomfort the patient during the cleaning of his teeth. In the event that the ratio of the volume of cleaning-liquid being supplied is about equal to the volume of cleaning-liquid being discharged, it is detected by the cleaning-liquid vacuuming-and-discharging device that the cleaning-liquid within the oral cavity is being fully discharged by the cleaning-liquid vacuuming-and-discharging device and thus deactivates the cleaning-liquid discharging device, thus making it possible for the cleaning-liquid discharging device to be activated only as needed, thus reducing wastage of electricity in powering the dental ultrasonic cleaning device and efficiently enhancing the ultrasonic cleaning.

The eighth aspect of this invention refers to a method for cleaning teeth or dentures ultrasonically by emitting ultrasonic waves through a cleaning-liquid to a surface of teeth or dentures as a cleaning-target in an oral cavity, characterized in that the cleaning-liquid is supplied to the liquid-reservoir part surrounding the ultrasonic-wave emitting surface of the ultrasonic-wave propagating unit, and that ultrasonic waves are emitted whilst the cleaning-liquid is in contact with the teeth or dentures as the cleaning-target, with the cleaning-liquid temporarily being reserved between the ultrasonic-wave emitting surface and the surface of the cleaning target, and with the cleaning-liquid being vacuumed off from a different surface of the cleaning-target.

The eighth aspect of this invention lets the cleaning-liquid be supplied to the liquid-reservoir part and reserved there temporarily between the ultrasonic-wave emitting surface at the tip-end of the ultrasonic-wave propagating unit and the surface of the cleaning-target. Ultrasonic waves are propagated from the ultrasonic-wave propagating unit and emitted to the surface of the cleaning-target through the cleaning-liquid being reserved in the liquid-reservoir part, thus ultrasonically cleaning that surface of the cleaning-target. At the same time, the cleaning-liquid is being vacuumed off a different surface of the cleaning-target and going into the embrasures of the cleaning-target so that the ultrasonic-waves propagating through the cleaning-liquid are working within the embrasures too in cleaning the lateral side of the cleaning-target efficiently as well as the surface of the cleaning-target.

Effect of the Invention

As detailed above, the first to eight aspects of this invention make it possible to efficiently clean the teeth or dentures in the oral cavity by using ultrasonic waves.

MODES FOR CARRYING OUT THE INVENTION (The First Embodiment)

Hereinafter, the first embodiment of the dental ultrasonic cleaning device of this invention is described in reference to the drawings.

Figure 1:
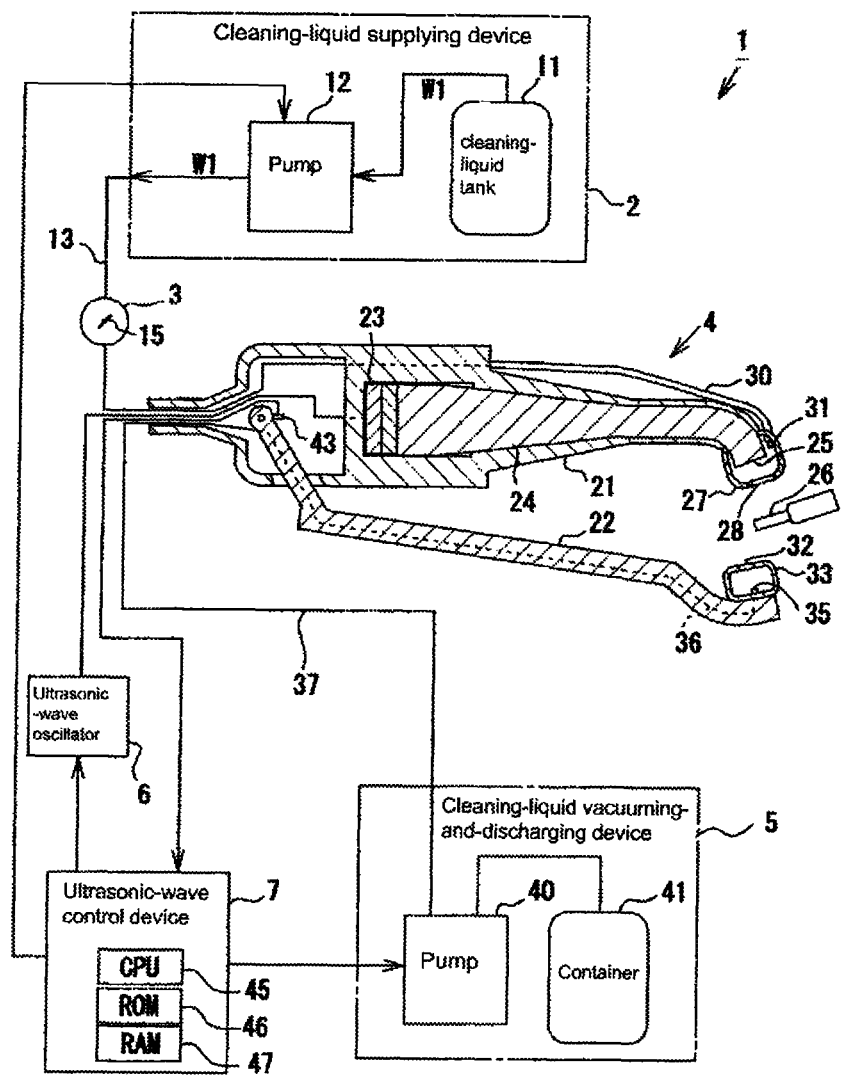
FIG. 1 is an explanatory diagram showing the first embodiment of the dental ultrasonic cleaning device.

FIG. 1 is an explanatory diagram showing the embodiment of the dental ultrasonic cleaning device 1. As shown in FIG. 1, the dental ultrasonic cleaning device 1 comprises a cleaning-liquid supplying device 2, a liquid-flow controller 3, a handpiece 4, a cleaning-liquid vacuuming-and-discharging device 5, an ultrasonic-wave oscillator 6, and an ultrasonic-wave control device 7. The dental ultrasonic cleaning device 1 allows for the ultrasonic cleaning of the teeth or dentures by emitting ultrasonic waves through a cleaning-liquid W1 (i.e. the cleaning water) to the surfaces of teeth or dentures as the cleaning-target in the oral cavity.

The cleaning-liquid supplying device 2 comprises a cleaning-liquid tank 11 for reserving the cleaning-liquid W1 and a pump 12 that is connected to the cleaning-liquid tank 11. The handpiece 4 is connected to the cleaning-liquid supplying device 2 by a supply-tube 13. The pump 12 when activated makes it possible to supply the cleaning-liquid W1 from the cleaning-liquid tank 11 to the handpiece 4.

The liquid-flow controller 3 provided in the way of the supply-tube 13 connecting the cleaning-liquid supplying device 2 to the handpiece 4 comprises a controller-tab 15 for adjusting the flow of the cleaning-liquid W1 being supplied to the handpiece 4, according to the operating range of the controller-tab 15.

The handpiece 4 is a graspable device shaped like a stapler that comprises an upper case 21 as the main-arm unit and a lower case 22 as the secondary-arm unit. A disk-shaped ultrasonic-wave transducer 23 for generating the ultrasonic waves and an ultrasonic-wave horn 24 (ultrasonic-wave propagating unit) for propagating the ultrasonic waves to the tip-end of the upper case 21 are stored within the upper case 21. The diameter of the ultrasonic-wave transducer 23 for instance is 30 mm and generates ultrasonic waves at 57 kHz frequency. The ultrasonic-wave horn 24 is shaped having a reduced-end that is bent, with the tip-end as the embodiment of this invention being bent at an angle of 5 to 90 degrees with respect to the central axis of the base-end of the ultrasonic-wave horn 24.

A vibratory surface 25 is provided on the tip-end of the ultrasonic-wave horn 24 as well as a liquid-reservoir part 27 that lets the cleaning-liquid W1 intervene between the vibratory surface 25 and the surface of the cleaning-target 26 (e.g. the teeth). The liquid-reservoir part 27 consists of a transparent-rubber material that surrounds the vibratory surface 25 of the tip-end of the ultrasonic-wave horn 24. Also, an opening part 28 is provided on the liquid-reservoir part 27 that faces the vibratory surface 25 of the ultrasonic-wave horn 24 to let the cleaning-liquid W1 make contact with the cleaning-target 26, thus blocking the opening part 28 and making it possible for the cleaning-liquid W1 to be reserved temporarily between the surface of the vibratory surface 25 and the cleaning-target 26.

Within the upper case 21, there is closely provided along the external surface of the ultrasonic-wave horn 24 and extending to the tip-end of the horn 24 a liquid-supply tube 30 (the cleaning-liquid supplying part) that is connected to the supply-tube 13, with the tip-end of the liquid-supply tube 30 being connected to the liquid-reservoir part 27 at the tip-end of the ultrasonic-wave horn 24 to supply the cleaning-liquid W1 into the liquid-reservoir part 27 through the liquid-supply outlet 31 provided at the end of the liquid-supply tube 30.

Regarding the handpiece 4, the base-end of the lower case 22 is rotatably connected to the upper case 21. A rubber cap-member 33 (the cleaning-liquid vacuuming part) having an opening part 32 is provided at the tip-end of the lower case 22. The cap-member 33 is provided at a certain interval opposite the liquid-reservoir part 27. The handpiece 4 is made to grip the cleaning-target 26 between the cap-member 33 at the tip-end of the lower case 22 and the liquid-reservoir part 27 at the tip-end of the upper case 21. Within the cap-member 33 there is a cleaning-liquid discharge-tube inlet 35 connected to the end of a suction tube 36 for vacuuming and discharging the spent cleaning-liquid W1.

Regarding this embodiment, the liquid-reservoir part 27 and the cap-member 33 are sized (e.g. about 10 mm in width) to surround a tooth and part of an adjoining tooth (the interdental space). The opening part 28 of the wall of the liquid-reservoir part 27 is 5 mm to 20 mm from the vibratory surface 25 of the ultrasonic-wave horn 24. As the cleaning-target 26 is being gripped by the cap-member 33 and by the liquid-reservoir part 27, the gap between the vibratory surface 25 of the ultrasonic-wave horn 24 and the surface of the cleaning-target 26 becomes 3 mm to 10 mm (5 mm regarding this embodiment), since the liquid-reservoir part 27 bows inwardly.

A suction tube 36 is stored longitudinally within the lower case 22 and is connected to a vacuuming pipe 37 applied to the base-end of the handpiece 4, and then it is connected to the cleaning-liquid vacuuming-and-discharging device 5 by the vacuuming pipe 37. The cleaning-liquid vacuuming-and-discharging device 5 comprises a pump 40 and a container 41 that is connected to the pump 40 for collecting the cleaning-liquid W1. Regarding the cleaning-liquid vacuuming-and-discharging device 5, in activating the pump 40 the cleaning-liquid W1 is vacuumed through the opening part 32 of the cap-member 33 and finally discharged into the container 41 through the suction tube 36 and the vacuuming pipe 37.

The pump 40 of the cleaning-liquid vacuuming-and-discharging device 5 is a vacuum pump. When the pump 40 is activated, the vacuuming-air pressure of the device 5 falls below atmospheric pressure, thus generating a vacuum in the vacuuming pipe 37 and the suction tube 36. Regarding this embodiment, the driving performance of the pump 12 and of the pump 40 is set such that the discharging-power of the cleaning-liquid W1 of the cleaning-liquid vacuuming-and-discharging device 5 is greater than the supplying-power of the cleaning-liquid W1 of the cleaning-liquid supplying device 2.

An activating-switch 43 (sensing-means) is provided on the base-end of the lower case 22, which is connected to the upper case 21, for detecting the rotation-angle of the lower case 22 that rotates when gripping the cleaning-target 26. The activating-switch 43 switches on when the rotation-angle of the lower case 22 is below the set value and switches off when the rotation-angle exceeds the set value. The activating-switch 43 is connected electrically to the ultrasonic-wave control device 7, and the control device 7 reads the sensing-signal of the activating-switch 43.

An ultrasonic-wave oscillator 6 is connected electrically to an ultrasonic-wave transducer 23 that is stored within the upper case 21. When the activating-signal of a certain oscillating-frequency is emitted, the ultrasonic-wave transducer 23 is activated. As such, the ultrasonic-wave transducer 23 generates ultrasonic waves corresponding to the oscillating-frequency of the ultrasonic-wave oscillator 6. Regarding this embodiment, approximately 8W of electricity on average is supplied from the ultrasonic-wave oscillator 6 to the ultrasonic-wave transducer 23. The oscillating-frequency of the ultrasonic-wave oscillator is 57 kHz.

The ultrasonic-wave control device 7 comprises a well-known computer such as a CPU 45, a ROM 46, or a RAM 47 or the like that controls the ultrasonic-wave oscillator 6 and cleaning-liquid supplying device 2 and cleaning-liquid vacuuming-and-discharging device 5 according to the detection-result of the activating-switch 43.

Regarding the embodiment of this invention, home-use electrical power (drawing omitted) for instance is used as the electrical-source for the dental ultrasonic cleaning device 1. However, it is possible to replace such an electrical-source for the ultrasonic cleaning device 1 with a battery, thus making it possible to use the ultrasonic cleaning device 1 even in a place without home-use electrical power.

Next is the method for cleaning and removing plaque that is adhered to the embrasures by using the dental ultrasonic cleaning device 1 of the embodiment of this invention.

Figure 2:
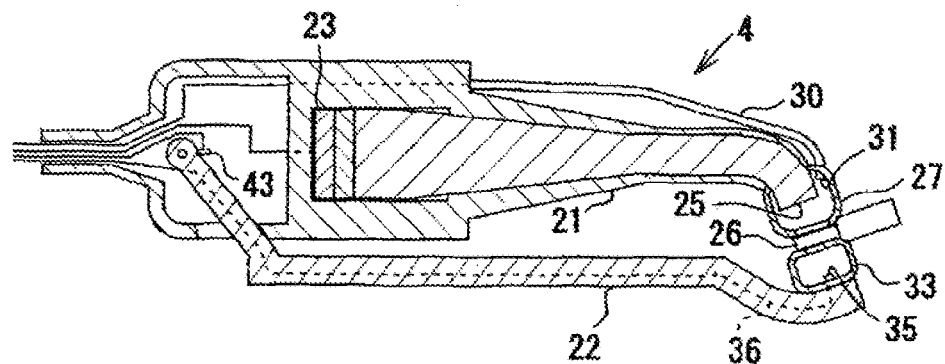
FIG. 2 is a diagram explaining the method of the ultrasonic cleaning.

An operator (specifically a dentist) operates the handpiece 4 by one hand in gripping within the oral cavity the cleaning-target 26 (e.g. the embrasures or the like filled with plaque) between the liquid-reservoir part 27 at the tip-end of the upper case 21 and the cap-member 33 at the tip-end of the lower case 22. (See FIG. 2) In this case, the rotation-angle of the base-end of the lower case 22 with respect to the upper case 21 becomes less than the set value, thus causing the activating-switch 43 to switch on. The ultrasonic-wave control device 7 reads the detection-signal of the activating-switch 43 and drives the pump 12 of the cleaning-liquid supplying device 2 and pump 40 of the cleaning-liquid vacuuming-and-discharging device 5 respectively. As such, the cleaning-liquid W1 is supplied from the cleaning-liquid supplying device 2 through the supply-tube 13 to the handpiece 4. Then, the cleaning-liquid W1 is supplied through the liquid-supply tube 30 within the handpiece 4 to the liquid-reservoir part 27, at which time the operator, by operating the controller-tab 15 of the liquid-flow controller 3, adjusts the volume of cleaning-liquid W1 being supplied.

As a certain period of time passes after the pump 12 and pump 14 are activated, after the cleaning-liquid W1 is sufficiently supplied within the liquid-reservoir part 27, the ultrasonic-wave control device 7 allows the ultrasonic-wave oscillator 6 to emit the activating-signal to the ultrasonic-wave transducer 23, causing it to vibrate and emit the 57 kHz ultrasonic waves that then propagate through the ultrasonic-wave horn 24 and emit from the vibratory surface 25 at the tip-end of the horn 24 and through the cleaning-liquid W1 It the cleaning-target 26.

The cleaning-liquid W1 seeping through the opening 28 of the liquid-reservoir part 27 flows through the embrasures and onto the surfaces of the teeth and is finally vacuumed through the opening 32 and into the cap-member 33 provided at the tip-end of the lower case 22, at which time the ultrasonic waves propagating through the cleaning-liquid W1 are efficiently working within the embrasures, on the surfaces of the teeth, removing plaque or the like. The cleaning-liquid W1 being vacuumed into the cap-member 33 continues through the suction tube 36 and through the vacuuming pipe 37 and then is discharged into the container 41 of the cleaning-liquid vacuuming-and-discharging device 5.

The operator working the handpiece 4, after a certain period of time has passed (e.g. 15 seconds), releases the liquid-reservoir part 27 of the upper case 21 and the cap-member 33 of the lower case 22 from the cleaning-target 26 and removes the handpiece 4 from the oral cavity, at which time the rotation-angle of the lower case 22 in respect to the upper case 21 exceeds the set value, and the activating-switch 43 switches off. The ultrasonic-wave control device 7 then stops the ultrasonic-wave oscillator 6 according to the detection-signal of the activating-switch 43, whilst at the same time stopping the pump 12 and pump 40 of the cleaning-liquid supplying device 2 and cleaning-liquid vacuuming-and-discharging device 5 respectively. The whole procedure completes the ultrasonic cleaning of the surfaces of the teeth as the cleaning-target 26.

Figure 3:
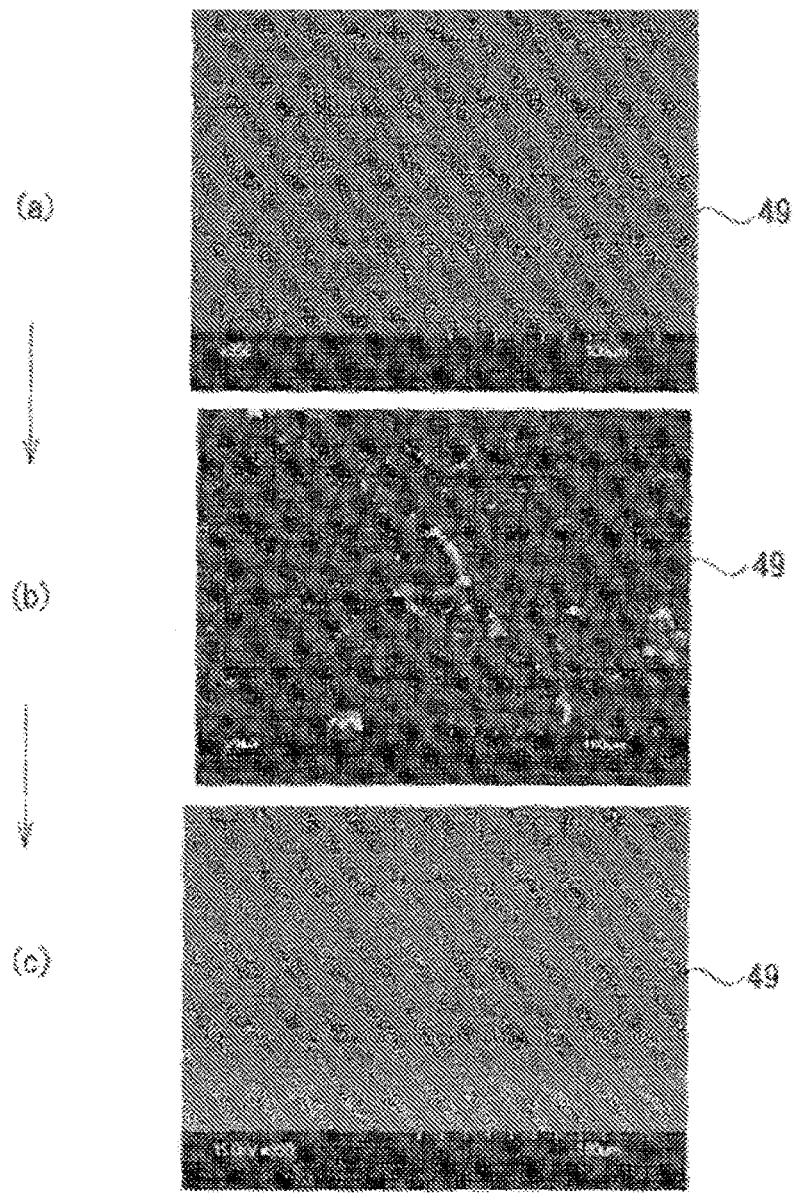
FIG. 3 is an explanatory diagram showing a scanning electron-microscope (SEM) photograph of the test-piece before and after the ultrasonic cleaning.

The inventors of this invention conducted a test to make sure of the effectiveness of the dental ultrasonic cleaning device 1 in removing plaque. Specifically, they affixed a test-piece of a dental light polymerized-resin on a removable-denture attachment and put it in the oral cavity of a test-subject for three days to let plaque form on the surface of the removable-denture. Three days later, they ultrasonically cleaned the surface of the test-piece on which plaque had formed, thus verifying the effectiveness of the dental ultrasonic cleaning device 1. The condition of this cleaning-test was that there be a 5 mm-gap between the vibratory surface 25 of the ultrasonic-wave horn 24 and the surface of the test-piece, and that the ultrasonic waves be emitted for 15 seconds at 57 kHz using 8W of electricity. The surface of the test-piece before and after the cleaning-test was observed through a scanning electron microscope (SEM). The result of the cleaning-test is shown in FIG. 3. The SEM photographs of FIG. 3 shows (a) the test-piece 49 before plaque had formed, (b) the test-piece 49 after plaque had formed, and (c) the test-piece after the ultrasonic cleaning had been done. As shown in FIG. 3 (a) to (c), it was proved that the plaque that had formed on the test-piece 49 had been completely removed by the ultrasonic cleaning.

Therefore, the embodiments of this invention realize the following effects.

(1) The dental ultrasonic cleaning device 1 as the embodiment of this invention allows for the cleaning-liquid W1 within the liquid-reservoir part 27 to be supplied there through the liquid-supply tube 30 and temporarily reserved between the vibratory-surface 25 at the tip-end of the ultrasonic-wave horn 24 and the surface of the cleaning-target 26. The ultrasonic waves generated by the ultrasonic-wave transducer 23 are transferred through the ultrasonic-wave horn 24 and emitted from the vibratory surface 25 and then go through the cleaning-liquid W1 within the liquid-reservoir part 27 to the surfaces of the cleaning-target 26, ultrasonically cleaning them. The cleaning-liquid W1 goes into the embrasures of the teeth or dentures as the cleaning-target 26 and then is vacuumed through the opening 32 of the cap-member 33 provided behind the cleaning-target 26 and is finally discharged from the oral cavity by going through the suction tube 36. At this time, the ultrasonic waves propagating through the cleaning-liquid W1 are efficiently working in the embrasures, cleaning the sides of the cleaning-target 26, whilst the pressure of the cleaning-liquid W1 flowing through the embrasures is cleansing the dirt from the surfaces of the teeth.

(2) The dental ultrasonic cleaning device 1 as the embodiment of this invention allows for the ultrasonic cleaning of the cleaning-target 26 whilst being gripped between the liquid-reservoir part 27 at the tip-end of the upper case 21 and the cap-member 33 at the tip-end of the lower case 22. In this case, even with the cleaning-target 26 being pressed with a certain amount of pressure by the liquid-reservoir part 27, such pressure is oppositely supported by the cap-member 33, thus avoiding the problem of the cleaning-target 26 moving due to one-way pressure being applied against it. Also, the handpiece 4 of the embodiment of this invention is shaped like a stapler of which the base-end of the lower case 22 is rotatably connected to the upper case 21, so letting the operator such as a dentist or the like hold the handpiece 4 single-handedly in rotating the lower case 22 to grip the cleaning-target 26 easily between the liquid-reservoir part 27 and the cap-member 33, thus improving the operability of the dental ultrasonic cleaning device 1 in conducting the cleaning operation quickly.

(3) The dental ultrasonic cleaning device 1 as the embodiment of this invention allows for the rotation-angle of the lower case 22, whilst the cleaning-target 26 is being gripped, to be detected by the activating-switch 43 and for the detection-result to be transmitted to the ultrasonic-wave control device 7. When the rotation-angle of the lower case 22 is below the set value, the cleaning-liquid supplying device 2 and the ultrasonic-wave oscillator 6 and the cleaning-liquid 26 vacuuming-and-discharging device 5 are activated. On the other hand, when the rotation-angle of the lower case 22 exceeds the set value, the cleaning-liquid supplying device 2 and the ultrasonic-wave oscillator 6 and the cleaning-liquid vacuuming-and-discharging device 5 are deactivated, in which case with the cleaning-target 26 in the grip of the cap-member 33 and liquid-reservoir part 27, the ultrasonic cleaning directly starts. Upon the cleaning-target 26 being released from the grip of the cap-member 33 and liquid-reservoir part 27, the ultrasonic cleaning directly stops. As such, whilst the cleaning-target 26 is being gripped, the dental ultrasonic cleaning device 1 will never wrongly start, thus reducing wastage of both electricity and cleaning-liquid and avoiding the problem of ultrasonic waves being emitted to an area other than the cleaning-target 26.

(4) The dental ultrasonic cleaning device 1 as the embodiment of this invention has a structure of which the liquid-reservoir part 27 surrounds the vibratory surface 25 of the ultrasonic-wave horn 24, so that the vibratory surface 25 does not directly touch the cleaning-target 26. Specifically, as the cleaning-target 26 is being gripped, there is realized about a 5 mm-gap between the vibratory surface 25 and the surface of the cleaning-target 26, thus avoiding the problem of the vibratory surface 25 touching and so damaging the surface of the cleaning-target 26. Also, liquid-reservoir part 27 and cap-member 33 are made of an elastic rubber-like material that does not damage the surface of the cleaning-target 26 being gripped but surely affixes the vibratory surface 25 of the ultrasonic-wave born 24 to the cleaning-target 26.

(5) Of the dental ultrasonic cleaning device 1 as the embodiment of this invention, the liquid-reservoir part 27 is made as a surrounding-wall and of material to prevent the cleaning-liquid W1 from ever seeping through between the bristles of a brush as seen in the conventional art, thus making it possible to reserve the cleaning-liquid W1 surely between the vibratory surface 25 and the surface of the cleaning-target 26. Also, since the liquid-reservoir part 27 is made of a transparent-rubber material, it is easily possible to be sure that the cleaning-liquid W1 is intervened between the vibratory surface 25 and the surface of the cleaning-target 26 within the liquid-reservoir part 27.

(6) Of the dental ultrasonic cleaning device 1 as the embodiment of this invention, the tip-end of the ultrasonic-wave horn 24 is bent, thus causing the vibratory surface 25 provided thereon to face the surface of the cleaning-target 26, thus surely making the ultrasonic waves to work on the surface of the cleaning-target 26.

(7) Of the dental ultrasonic cleaning device 1 as the embodiment of this invention, the capacity of the cleaning-liquid vacuuming-and-discharging device 5 in discharging the cleaning-liquid W1 is greater than the capacity of the cleaning-liquid supplying device 2 in supplying the cleaning-liquid W1, so that during the ultrasonic cleaning the cleaning-liquid W1 does not remain in the oral cavity but surely discharges.

(8) Of the dental ultrasonic cleaning device 1 as the embodiment of this invention, the ultrasonic-wave control device 7 activates the ultrasonic-wave oscillator 6 more slowly than it does the cleaning-liquid supplying device 2, so that the ultrasonic waves are emitted after the cleaning-liquid W1 is sufficiently reserved in the liquid-reservoir part 27, so preventing the ultrasonic waves being emitted before the cleaning-liquid W1 is within the liquid-reservoir part 27, thus letting the ultrasonic cleaning be efficiently conducted.

(Second Embodiment)

Hereinafter, the second embodiment of this invention is described in reference to the drawings. The dental ultrasonic cleaning device 1A as the embodiment of this invention is different from the above first embodiment of this invention in respect to the structure that discharges the cleaning-liquid W1 from the liquid-reservoir part 27. If the embrasure of the cleaning-target 26 is small, the cleaning-liquid W1 will not flow smoothly through the embrasure to the cap-member 33, in which case the cleaning-liquid W1 will not discharge sufficiently into the cap-member 33 and on through the suction tube 36. Also, the second embodiment of this invention has a structure such that the cleaning-liquid W1 is discharged from the liquid-reservoir part 27.

Figure 4:
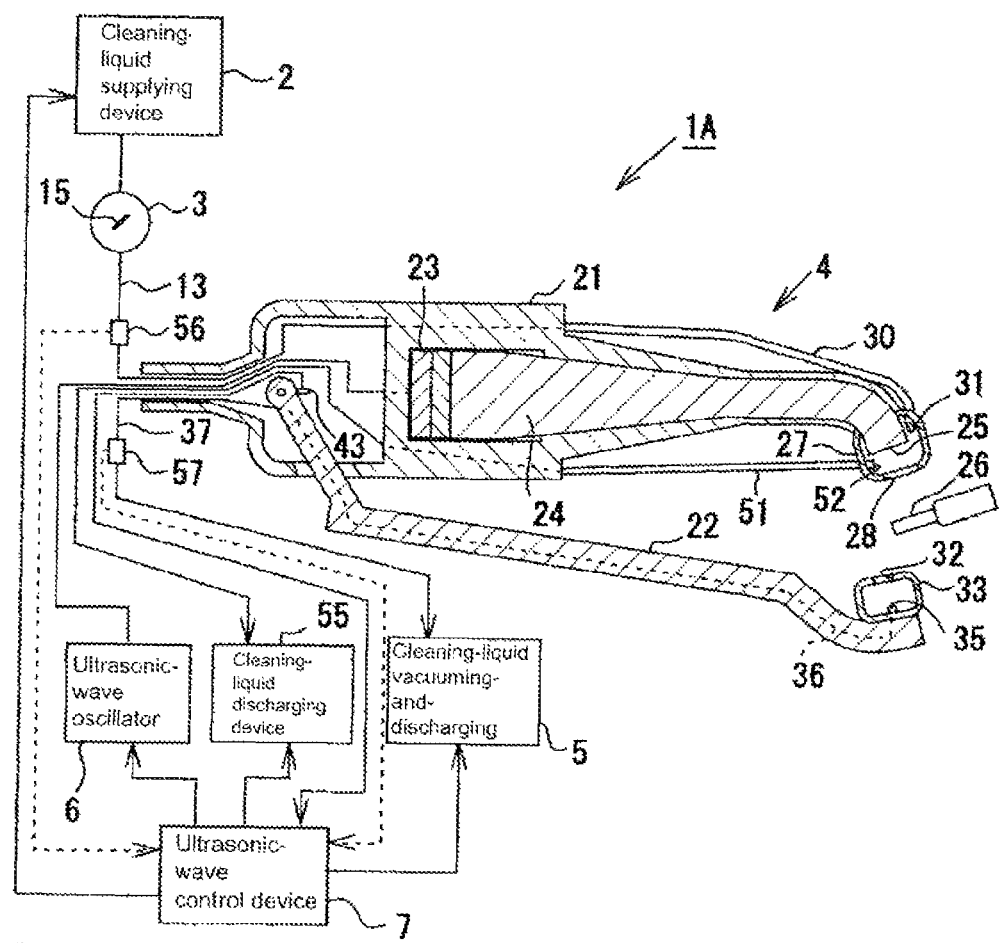
FIG. 4 is an explanatory diagram showing the second embodiment of the dental ultrasonic cleaning device.

Specifically, as shown in FIG. 4, the dental ultrasonic cleaning device 1A as the embodiment of this invention has a structure of which a cleaning-liquid discharge tube 51 is provided closely along the external surface of the ultrasonic-wave horn 24 and extends to the tip-end of the ultrasonic-wave horn 24 within the upper case 21, and that the end of the cleaning-liquid discharge tube 51 is connected to the liquid-reservoir part 27. A cleaning-liquid discharge-tube inlet 52 is provided at the end of the cleaning-liquid discharge tube 51 within the liquid-reservoir part 27. The base-end of the cleaning-liquid discharge tube 51 is connected to the cleaning-liquid discharging device 55. By activating the pump (not shown in the drawing) of the cleaning-liquid discharging device 55, the cleaning-liquid W1 being reserved within the liquid-reservoir part 27 is vacuumed into the cleaning-liquid discharge-tube inlet 52 of the cleaning-liquid discharge tube 51. A cleaning-liquid supply-measuring device 56 (e.g. ultrasonic flow-meter) is provided in the way of the supplying pipe 13 for measuring the volume of cleaning-liquid W1 flowing to the handpiece 4. The cleaning-liquid supply-measuring device 56 measures the volume of cleaning-liquid W1 being supplied through the supplying pipe 13 to the liquid-reservoir part 27 in units per time, during a certain period of time, and transmits the measurement-data to the ultrasonic-wave control device 7. A cleaning-liquid discharge-measuring device 57 (e.g. ultrasonic flow-meter) is provided in the way of the vacuuming pipe 37 for measuring the volume of cleaning-liquid W1 being discharged from the handpiece 4 to the cleaning-liquid vacuuming-and-discharging device 5. The cleaning-liquid discharge-measuring device 57 measures the volume of cleaning-liquid W1 being discharged through the vacuuming pile 37 in units per time, during a certain period of time, and transmits the measurement-data to the ultrasonic-wave control device 7.

The ultrasonic-wave control device 7 controls the cleaning-liquid discharging device 55 according to the ratio of the volume of cleaning-liquid W1 being supplied to that being discharged. Specifically, when the volume of cleaning-liquid W1 being discharged is less than that being supplied, the cleaning-liquid W1 does not sufficiently discharge into the opening 32 of the cap-member 33 and through the suction tube 36 but remains in the oral cavity. In this case, by both the cleaning-liquid discharging device 55 and the cleaning-liquid vacuuming-and-discharging device 5 being activated, the cleaning-liquid W1 discharges into the cleaning-liquid discharge-tube inlet 52 of the liquid-reservoir part 27 and through the cleaning-liquid discharge tube 51. As such, by both discharging devices being activated, a sufficient volume of cleaning-liquid W1 is discharged, thus avoiding the problem of too much cleaning-liquid collecting in the oral cavity, which would discomfort the subject (e. g. patient) during the cleaning of his teeth.

If the ratio of the volume of cleaning-liquid W1 being supplied is about equal to that being discharged, such is detected by the cleaning-liquid vacuuming-and-discharging device 5 that the cleaning-liquid W1 within the oral cavity is being fully discharged, and the cleaning-liquid discharging device 55 is deactivated. Thus, it is possible that the cleaning-liquid discharging device 55 be activated only as needed, thus reducing wastage of electricity in powering the dental ultrasonic cleaning device 1A and efficiently enhancing the ultrasonic cleaning.

The embodiment of this invention can be modified as follows.

The above referenced dental ultrasonic cleaning device 1 and 1A comprise a mutual structure of which the handpiece 4 consists of an upper case 21 and a lower case 22 by which to grip the cleaning-target 26, but the device 1 and 1A are not limited to such a structure. It is possible for example that the lower case 22 be omitted and that a suction tube be provided extending from the bottom of the upper case 21, wherein a cleaning-liquid vacuuming part provided at the tip-end of the suction tube is aligned to face the liquid-reservoir part 27. In this case, it would be possible to use as added force such a spring or the like to grip the cleaning-target 26 by and between the cleaning-liquid vacuuming part of the suction tube and the liquid-reservoir part 27.

The above referenced dental ultrasonic cleaning device 1 and 1A comprise a mutual structure of which the activating-switch 43 provided at the base-end of the lower case 22 detects the status of the cleaning-target 26 as being gripped, thus governing the cleaning-liquid supplying device 2 and ultrasonic-wave oscillator 6 or the like. However, the device 1 and 1A are not limited to such a structure. As a sensing-means to detect the status of the cleaning-target 26 as being gripped, it is possible for example to provide a pressure-sensor to detect whether a load is being added to the liquid-reservoir part 27 or to the cap-member 33 (at the tip-end of the lower case 22). Also, as another sensing-means, it is possible to provide a light-sensor to detect whether the detection-light is being blocked by the cleaning-target 26.

The above-referenced dental ultrasonic cleaning device 1 and 1A as the embodiments of this invention achieve the ultrasonic cleaning of the cleaning-target 26 being gripped. However, it is possible to modify such device 1 and 1A by providing a switch to start the cleaning of the cleaning-target 26 ultrasonically regardless of the status that it is being gripped. Specifically, it is possible to provide a foot-switch by which to activate the ultrasonic-wave oscillator 6 and to adjust the timing and duration of the ultrasonic waves being emitted from the ultrasonic-wave transducer 23. It is possible also to provide a cleaning-liquid supply-switch on the handpiece 4 for adjusting the timing of the cleaning-liquid W1 being supplied and for achieving the ultrasonic cleaning as the cleaning-target 26 is being gripped (e.g. when the activating-switch 43 is activated) on condition that the foot-switch or the cleaning-liquid supply-switch is switched on.

It is possible to provide a mode-switch on the ultrasonic-wave oscillator 6 for selecting the output-mode (continuous or burst) of the ultrasonic waves, thus making it possible during the ultrasonic cleaning to select the output-mode of the ultrasonic waves. Thus, when continuous-mode is selected, the ultrasonic-wave transducer 23 is continuously activated. When burst-mode is selected, the ultrasonic-wave transducer 23 is irregularly activated. As such, the ultrasonic cleaning is appropriately efficiently done according to the sum of contamination on the cleaning-target 26.

The above-referenced dental ultrasonic cleaning device 1 and 1A as the embodiments of this invention have a mutual structure of which the cleaning-liquid W1 is supplied to the liquid-reservoir part 27 through the liquid-supply tube 30 provided along the external surface of the ultrasonic-wave horn 24. However, the device 1 and 1A are not limited to such a structure. It is possible for example to provide a cleaning-liquid supply pipe for supplying the cleaning-liquid W1 on a place that is to be the center-axis of the ultrasonic-wave transducer 23 or of the ultrasonic-wave horn 24, thus supplying the cleaning-liquid W1 through such a cleaning-liquid supply pipe to the liquid-reservoir part 27.

It is also possible to configure the cleaning-liquid supplying device 2 of each embodiment as described above by incorporating a bubbling-device for bubbling carbon dioxide ($CO$) into the cleaning-liquid W1. As such, bubbling carbon dioxide into the cleaning-liquid W1 releases the air in the cleaning-liquid W1, thereby displacing it to the carbon dioxide, in which case it is possible to control the Oil radical (hydroxyl radical) produced by the emission of the ultrasonic waves into the cleaning-liquid W1. Generally, when propagating strong ultrasonic waves into the cleaning-liquid W1, cavitation occurs, and in the process of the compression and disruption of cavitation, a strong reaction field is formed. The temperature of the cavitation varies according to the type of gas existing in the liquid. The cavitation-temperature of a triatomic gas such as carbon dioxide or the like is lower than that of a monatomic or diatomic gas. As such, bubbling the carbon dioxide into the cleaning-liquid W1 makes it difficult to produce the OH radical, thus preventing a degradation-reaction (chemical reaction) by the OH radical. It is also possible to use a triatomic gas such as laughing gas ($N_2O$) or the like other than carbon dioxide ($CO_2$) to control the production of OH radicals.

The above-referenced dental ultrasonic cleaning device 1 and 1A as the embodiments of this invention comprise a special cleaning-liquid vacuuming-and-discharging device 5 and cleaning-liquid discharging device 55, but the device 1 and 1A are not limited to such. For example, a dental-treatment unit that is equipped with a vacuum-device or an electric-pump vacuum tube can be used, and it is possible to connect the suction tube 36 or the cleaning-liquid discharge tube 51 of the handpiece 4 to a vacuum-device or an electric-pump vacuum tube to use as ultrasonic cleaning device 1 and 1A. A hospital bed that is equipped with a vacuum tube can also be used. It is also possible to connect the suction tube 36 or the cleaning-liquid discharge tube 51 to an electric-pump vacuum tube to make an ultrasonic cleaning device 1 and 1A, thus using existing equipment to configure the ultrasonic cleaning device 1 and 1A and thereby reducing the cost of equipment.

The above-referenced dental ultrasonic cleaning device 1A as the second embodiment of this invention comprises the cleaning-liquid vacuuming-and-discharging device 5 and the cleaning-liquid discharging device 55. Alternatively, it is possible to make the two devices a mutually common cleaning-liquid discharging device. For example, it is possible to connect the base-end of the cleaning-liquid discharge tube 51, used in discharging the cleaning-liquid W1 from the liquid-reservoir part 27, to the cleaning-liquid vacuuming pipe 37 and to an on-off valve (not shown in drawing) that, upon activating it, the cleaning-liquid W1 is discharged from the liquid-reservoir part 27 through the cleaning-liquid discharge tube 51 and the vacuuming pipe 37 to the cleaning-liquid vacuuming-and-discharging device 5.

The above-referenced dental ultrasonic cleaning device 1A as the second embodiment of this invention comprises a structure of which the cleaning-liquid discharge-tube inlet 52 of the cleaning-liquid discharge tube 51 is provided within the liquid-reservoir part 27. However, it is possible to provide the cleaning-liquid discharge-tube inlet 52 near the liquid-reservoir part 27.

The above-referenced dental ultrasonic cleaning devices 1 and 1A as the embodiments of this invention comprise the liquid-reservoir part 27 being made of a transparent-rubber material, but it is not limited to being made of such material. It is possible to use a colored flexible-resin, and the rubber cap-member 33 can be replaced by a flexible-resin, as well as can the liquid-reservoir part 27.

Figure 5:
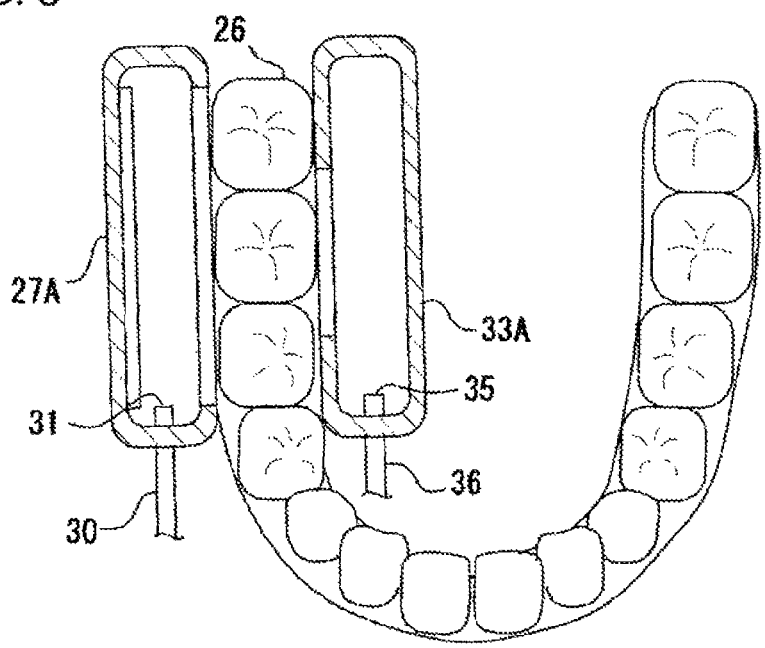
FIG. 5 is an explanatory diagram showing another embodiment of the liquid-reservoir part and the cap member.

As shown in FIG. 5, it is possible to configure the cap-member 33A and the liquid-reservoir part 27A having a sufficient size to surround a number of neighboring teeth (e.g. two or more teeth), thus making it possible to clean more than one cleaning-target 26 ultrasonically at the same time, thus improving the efficiency of the cleaning.

The above-referenced ultrasonic cleaning devices 1 and 1A as embodiments of this invention comprise an ultrasonic-wave oscillator 6 having an oscillating-frequency of 57 kHz, but it is not limited to that. It is possible to change the frequency accordingly to one in the range of from 20 kHz to 1 MHz to do the ultrasonic cleaning efficiently.

The above-referenced dental ultrasonic cleaning device 1 and 1A as the embodiments of this invention comprise an ultrasonic-wave horn 24 as the ultrasonic-wave propagating unit, shaped with a reducing end that is bent but not limited to being thus. It is possible for example that a rod-shaped ultrasonic-wave horn 24 be used of equal width without a bent-end, in which case it is preferable to provide an ultrasonic-wave emitting-surface on the tip-end of such a rod-shaped ultrasonic-wave horn, slanted at a certain angle (e.g. at 100 to 170 degrees) with respect to the central axis of the horn. Such an ultrasonic-wave emitting-surface should be formed on a place far from the focal position of an ultrasonic-wave transducer to make it possible to emit comparatively higher ultrasonic-waves such as at 1 MHz. Thus, the ultrasonic cleaning could be done with a regular and soft ultrasonic-intensity.

Besides the technical ideas of this invention, as described above, other technical ideas to be understood are described hereinafter.

(1) A dental ultrasonic cleaning device according to any one of the first to seventh aspect of this invention is characterized in that the liquid-reservoir part is made of a flexible resin material.

(2) A dental ultrasonic cleaning device according to any one of the first to seventh aspects of this invention is characterized in that the liquid-reservoir part is a surrounding-wall member made of a flexible resin material.

(3) A dental ultrasonic cleaning device according to any one of the first to seventh aspects of this invention is characterized in that the liquid-reservoir part is a surrounding-wall member made of a transparent-rubber.

(4) A dental ultrasonic cleaning device according to any one of the first to seventh aspects of this invention is characterized in that the cleaning-liquid vacuuming part is a rubber cap-member with an opening.

(5) A dental ultrasonic cleaning device according to any one of the first to seventh aspects of this invention is characterized in that the teeth or dentures as the cleaning-target are more than one, and that the liquid-reservoir part is sized to surround a number of neighboring teeth or dentures at the same time.

(6) A dental ultrasonic cleaning device according to any one of the first to seventh aspects of this invention is characterized in that the teeth or dentures as the cleaning-target are more than one, and that the rubber cap-member as the cleaning-liquid vacuuming part is sized to surround a number of neighboring teeth or dentures at the same time.

(7) A dental ultrasonic cleaning device according to any one of the first to seventh aspects of this invention is characterized in that the tip-end of the ultrasonic-wave propagating unit is bent at an angle of 5 to 90 degrees.

(8) A dental ultrasonic cleaning device according to any one of the first to seventh aspects of this invention is characterized in that the gap between the ultrasonic-wave emitting surface of the ultrasonic-wave propagating unit and the cleaning-target is 3 mm to 10 mm.

(9) A dental ultrasonic cleaning device according to the above technical idea (2) or (3) is characterized in that the gap between the ultrasonic-wave emitting surface of the ultrasonic-wave propagating unit and the opening of the surrounding-wall member is 5 mm to 20 mm.

(10) A dental ultrasonic cleaning device according to the third aspect of this invention is characterized in that the oscillating frequency of the ultrasonic-wave oscillator is 20 kHz to 1 MHz.

(11) A dental ultrasonic cleaning device according to the third aspect of this invention is characterized in that the vacuuming pressure of the cleaning-liquid vacuuming-and-discharging device is lower than the atmospheric pressure.

(12) A dental ultrasonic cleaning device according to the third aspect of this invention is characterized in that the discharge-capacity of the cleaning-liquid vacuuming-and-discharging device is greater than the supply-capacity of the cleaning-liquid supplying device.

(13) A dental ultrasonic cleaning device according to the seventh aspect of this invention is characterized in that the ultrasonic-wave control device activates the cleaning-liquid discharging device when the volume of the cleaning-liquid being discharged is less than the volume of cleaning-liquid being supplied.

(14) A dental ultrasonic cleaning device according to the third aspect of this invention is characterized in that a start-switch is provided for the operator to start the ultrasonic cleaning and the aforementioned ultrasonic-wave control device governing the ultrasonic-wave oscillator, the cleaning-liquid supplying device, and the cleaning-liquid vacuuming-and-discharging device.

(15) A dental ultrasonic cleaning device according to the third aspect of this invention is characterized in that the ultrasonic-wave control device activates the ultrasonic-wave oscillator more slowly than it does the cleaning-liquid supplying device.

(16) A dental ultrasonic cleaning device according to the third aspect of this invention is characterized in that the sensing-means is a pressure-sensor for detecting a load added to the liquid-reservoir part or to the cleaning-liquid vacuuming part at the tip-end of the secondary-arm unit.

(17) A dental ultrasonic cleaning device according to the third aspect of this invention is characterized in that the sensing-means is a light-sensor for detecting whether the detection-light is being blocked by the cleaning target.

DESCRIPTION OF THE REFERENCE SIGNS

1, 1A: Dental ultrasonic cleaning device
2: Cleaning-liquid supplying device
4: Handpiece
5: Cleaning-liquid vacuuming-and-discharging device
6: Ultrasonic-wave oscillator
7: Ultrasonic-wave control device as the control device
21: Upper case as the main-arm unit
22: Lower case as the secondary-arm unit
23: Ultrasonic-wave transducer 24: Ultrasonic-wave horn as the ultrasonic-wave propagating unit
25: Ultrasonic-wave emitting surface as the vibratory-surface
27, 27A: Liquid-reservoir part as the liquid-reserving part
28: Opening
30: Liquid-supply tube as the cleaning-liquid supplying part
33, 33A: Cap-member as the cleaning-liquid vacuuming part
36: Suction tube
43: Activating-switch as the sensing-means
51: Cleaning-liquid discharge tube as the cleaning-liquid discharging part
52: Cleaning-liquid discharge-tube inlet
55: Cleaning-liquid discharging device
56: Cleaning-liquid supply-measuring device
57: Cleaning-liquid discharge-measuring device
W1: Cleaning-liquid

The invention claimed is:

1. A dental ultrasonic cleaning device for cleaning teeth or dentures ultrasonically by emitting ultrasonic waves through a cleaning-liquid to a cleaning-target comprising:
   an ultrasonic-wave transducer for generating the ultrasonic waves;
   an ultrasonic-wave pro propagating unit for propagating the ultrasonic waves to an ultrasonic-wave emitting surface at a tip-end side of the ultrasonic-wave propagating unit;
   a liquid-reservoir part for temporarily reserving the cleaning-liquid between a surface of the cleaning-target and the ultrasonic-wave emitting surface in a state of being in contact with the cleaning target, the liquid-reservoir part being provided in such a manner as to surround the ultrasonic-wave emitting surface;
   a liquid-supply tube for supplying the cleaning-liquid to the liquid-reservoir part;
   a suction tube having a liquid-suction pat and for sucking and draining the cleaning-liquid that had been used during the ultrasonic cleaning through the liquid-suction part, the liquid-suction part being disposed at a predetermined distance from the liquid reservoir part;
   a handpiece adapted to be handled by an operator, the handpiece comprising a main-arm unit to house the ultrasonic-wave transducer and the ultrasonic-wave propagating unit, and a secondary-arm unit having a tip-end portion by which the cleaning-target is gripped between the liquid-reservoir part at a tip-end of the main-arm unit and the secondary-arm unit, and a liquid-vacuuming part is provided at a tip-end of the secondary-arm unit;
   an ultrasonic-wave oscillator for activating the ultrasonic-save transducer;
   a cleaning-liquid supplying device for supplying the cleaning-liquid to the liquid-supply tube;
   a cleaning-liquid vacuuming-and-discharging device for vacuuming and discharging the cleaning-liquid through the suction tube;
   a sensor for detecting the cleaning-target being gripped by and between the liquid-reservoir part of the main-arm unit and the cleaning-liquid vacuuming part at the tip-end of the secondary-arm unit;
   a control device for controlling at least one of the ultrasonic-wave oscillator, the cleaning-liquid supplying device, or the cleaning-liquid vacuuming-and-discharging device, according to the detection by the sensor;
   wherein the handpiece has a stapler structure that the base-end of the secondary-arm unit is rotatably connected to the main-arm unit; and
   further wherein the sensor detects a rotation-angle of the secondary-arm unit and transmits a detection result to the control device for the control device to activate the ultrasonic-wave oscillator, the cleaning-liquid supplying device, and the cleaning-liquid vacuuming-and-discharging device when the rotation-angle of the secondary-arm unit is below a set value, or to deactivate the ultrasonic-wave oscillator, the cleaning-liquid supplying device, and the cleaning-liquid vacuuming-and-discharging device when the rotation-angle of the secondary-arm unit exceeds the set value.

2. A dental ultrasonic cleaning device according to claim 1, further comprising a cleaning-liquid discharge-tube inlet being provided within or near the liquid-reservoir part and through which the cleaning-liquid is discharged from the liquid-reservoir part.

3. A dental ultrasonic cleaning device according to claim 2, further comprising:
   a cleaning-liquid discharging device for discharging the cleaning-liquid through the cleaning-liquid discharge tube;
   a cleaning-liquid supply-measuring device for measuring a volume of cleaning-liquid being supplied per hour through the liquid-supply tube; and
   a cleaning-liquid discharge-measuring device for measuring a volume of cleaning-liquid being discharged per hour through the suction tube; and characterized in that the ultrasonic-wave control device reads data of the cleaning-liquid supply-measuring device about the volume of cleaning-liquid being supplied and data of the cleaning-liquid discharge-measuring device about the volume of cleaning-liquid being discharged, which then directs operation of the cleaning-liquid vacuuming-and-discharging device according to a ratio of the volume of cleaning-liquid being supplied to the volume of cleaning-liquid being discharged.

* * * * *